United States Patent
Buelna

(10) Patent No.: US 6,942,676 B2
(45) Date of Patent: Sep. 13, 2005

(54) SURGICAL CLAMP PADS WITH DEFLECTING ELEMENTS

(75) Inventor: Terrence Buelna, Santa Barbara, CA (US)

(73) Assignee: Novare Surgical Systems, Inc., Cupertino, CA (US)

(*) Notice: Subject to any disclaimer, the term of this patent is extended or adjusted under 35 U.S.C. 154(b) by 404 days.

(21) Appl. No.: 10/104,866

(22) Filed: Mar. 21, 2002

(65) Prior Publication Data

US 2003/0181932 A1 Sep. 25, 2003

(51) Int. Cl.[7] .............................................. A61B 17/08
(52) U.S. Cl. ...................... 606/158; 606/151; 606/157; 606/207
(58) Field of Search ............................. 606/157, 158, 606/205, 207

(56) References Cited

U.S. PATENT DOCUMENTS

| | | |
|---|---|---|
| 2,668,538 A | 2/1954 | Baker |
| 2,743,726 A | 5/1956 | Grieshaber |
| 3,446,211 A | 5/1969 | Markham |
| 3,503,396 A | 3/1970 | Pierie et al. |
| 3,503,397 A | 3/1970 | Fogarty et al. |
| 3,503,398 A | 3/1970 | Fogarty et al. |
| 3,515,139 A | 6/1970 | Mallina |
| 3,746,002 A | 7/1973 | Haller |
| 3,880,166 A | 4/1975 | Fogarty |
| 3,993,076 A | 11/1976 | Fogarty |
| 4,120,302 A | 10/1978 | Ziegler |
| 4,611,593 A | 9/1986 | Fogarty et al. |
| 4,821,719 A | 4/1989 | Fogarty |
| 5,171,253 A | 12/1992 | Klieman |
| 5,242,458 A | 9/1993 | Bendel et al. |
| 5,258,005 A | 11/1993 | Christian |
| 5,569,274 A | 10/1996 | Rapacki et al. |
| 5,591,182 A | 1/1997 | Johnson |
| 5,609,599 A | 3/1997 | Levin |
| 5,624,454 A | 4/1997 | Palti et al. |
| 5,674,220 A | 10/1997 | Fox et al. |
| 5,676,676 A | 10/1997 | Porter |
| 5,728,121 A | 3/1998 | Bimbo et al. |
| 5,855,590 A | 1/1999 | Malecki et al. |
| 6,007,552 A | 12/1999 | Fogarty et al. |
| 6,099,539 A | 8/2000 | Howell et al. |
| 6,299,621 B1 | 10/2001 | Fogarty et al. |
| 6,312,445 B1 | 11/2001 | Fogarty et al. |

FOREIGN PATENT DOCUMENTS

| | | |
|---|---|---|
| EP | 0490301 A1 | 6/1992 |
| WO | WO 98/33437 | 8/1998 |
| WO | 02/15805 A2 | 2/2002 |

*Primary Examiner*—Julian W. Woo
(74) *Attorney, Agent, or Firm*—Morrison & Foerster LLP

(57) ABSTRACT

A replaceable pad or insert for attachment to the jaw of a jaw-type occlusion device. The insert includes an elastomeric cushion with a deflecting element embedded in the cushion, providing for improved gripping of a clamped vessel while minimizing trauma to the vessel.

3 Claims, 1 Drawing Sheet

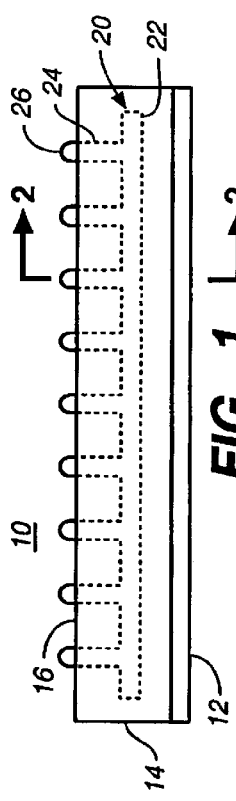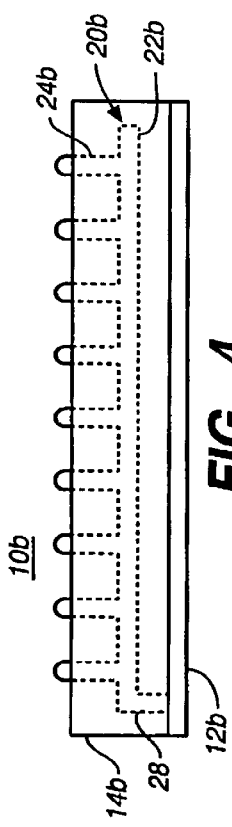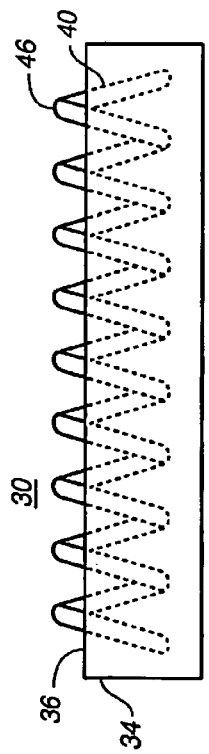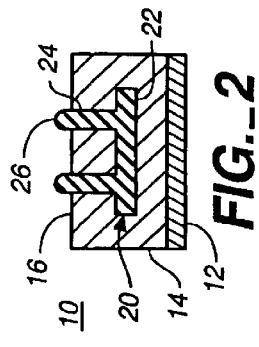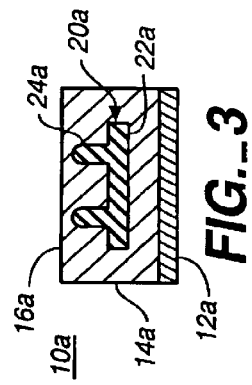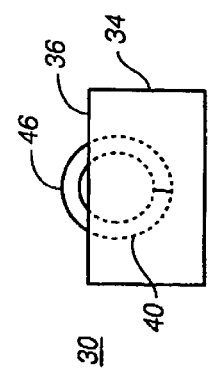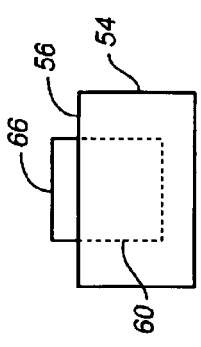

SURGICAL CLAMP PADS WITH DEFLECTING ELEMENTS

BACKGROUND OF THE INVENTION

The present invention relates generally to surgical instruments for occluding a vessel or other body conduit, and more particularly, to replaceable pads or inserts for attachment to jaw-type occlusion devices.

Instruments for occluding blood vessels and other body conduits are well known. Conventional surgical clamps or clips made of metal or other rigid materials can cause trauma to the clamped vessel at the clamping site. A number of atraumatic instruments have been developed for reducing trauma to a vessel during occlusion. In particular, conventional surgical clamps and clips have been adapted to include jaw surfaces containing resilient members or pads. These devices are prone to slipping off of the clamped vessel. This can be especially problematic in situations where, due to obstructions, a vessel has been clamped with only the distal tips of the clamp jaws. In such situations, the vessel can be especially prone to slipping in the direction of the distal tips.

Other attempts have been made to atraumatically occlude a vessel in a more secure fashion. U.S. Pat. No. 3,746,002 to Haller discloses a vascular clamp with resilient gripping members located on the jaws. A plurality of pin members are embedded within the gripping members, the pin members being of a length such that when a vessel is clamped between the members, the resilient material deflects to accommodate the vessel, exposing the pin members which grippingly engage the outer layer of the vessel, thus securing the vessel to the gripping member. While the Haller device is less traumatic to a vessel than other occlusion devices, it nevertheless has the disadvantage of traumatizing the outer layer of the vessel.

U.S. Pat. No. 3,515,139 to Mallina discloses surgical forceps with hard plastic inserts having spherical protuberances and complementary grooves or spherical cavities. U.S. Pat. No. 3,503,397 to Fogarty discloses surgical clamps with jaw inserts having hard plastic teeth along the edges of the insert with a softer component along the interior of the insert. The hard teeth of this device serve to resist movement of a clamped vessel laterally of the jaw, but do so at increased risk of trauma to the vessel.

There is thus a need for a surgical clamp which atraumatically occludes vessels with improved gripping capabilities while simultaneously avoiding the disadvantages previously associated with existing surgical clamps or occlusion devices.

SUMMARY OF THE INVENTION

The present invention meets these and other needs and provides for replaceable surgical clamp pads or inserts having an attaching structure for attachment of the insert to the jaw, and an elastomeric cushion secured to the attaching structure. The cushion includes a clamping surface for engagement with a vessel or other body tissue, and a deflecting element, at least a portion of which is embedded within the cushion, between the attaching structure and the clamping surface. The deflecting element can also include a second portion that extends from the clamping surface.

In one embodiment of the invention, the deflecting plate further comprises an elongate plate embedded within the cushion and oriented in a plane generally parallel to the clamping surface. The plate can further include one or more columns extending generally perpendicular to the clamping surface, and portions of the columns may also extend from clamping surface. In a variation on this embodiment, one end of the deflecting plate can be maintained in a fixed relationship to the attaching structure.

In another embodiment of the invention, the deflecting element can further comprise a coil oriented longitudinally along the cushion length. The deflecting element can include portions of the spring that extend from the clamping surface of the pad.

In yet another embodiment of the invention, the deflecting element can further comprise folded pleats extending longitudinally along the cushion length. Again, portions of the folded pleats can extend from the clamping surface of the cushion.

Methods of manufacturing the replaceable pad or inserts of the present invention are also provided.

BRIEF DESCRIPTION OF THE DRAWINGS

FIG. 1 is a side view of an insert according to a first embodiment of the invention, showing a deflecting element embedded in a cushion;

FIG. 2 is a cross-section view of the insert of FIG. 1 taken on the plane designated by line 2—2 of FIG. 1;

FIG. 3 is a cross-section view of a modified version of the insert of FIG. 2;

FIG. 4 is a side view of an insert according to a second embodiment of the invention;

FIG. 5 is a side view of an insert according to a third embodiment of the invention;

FIG. 6 is an end view of the insert of FIG. 5;

FIG. 7 is a side view of an insert according to a fourth embodiment of the invention; and FIG. 8 is an end view of the insert of FIG. 7.

DETAILED DESCRIPTION OF THE INVENTION

FIGS. 1 and 2 depict a first embodiment of a replaceable surgical clamp pad or insert according to the invention. Insert 10 includes attachment member 12 for attaching the insert to the jaw of a jaw-type occlusion device. Elastomeric cushion 14 is secured to the attachment member. Cushion 14 includes a clamping surface 16 for engagement with a vessel or other body tissue, opposite the attachment member. Deflecting element 20 is embedded in the cushion.

Elastomeric cushion 14 can be formed of a variety of materials known in the art that are resiliently deflectable and which provide cushion to a clamped vessel. Such materials include, but are not limited to, natural rubber, neoprene, urethane, ethyl vinyl acetate foam, or silicone or silicone foam. It is desirable that the material be a thermoplastic elastomer suitable for liquid injection molding and having a 20A–40 A shore durometer rating. Such thermoplastic elastomers include silicone, such as GE 6040 or silicone foam GE RTF762, polyurethane, and KRATON™ (Shell Chemicals Ltd.)

The elastomeric cushions of the invention can be formed in a variety of sizes and shapes. In general the cushions will conform to, or be conformable to, the jaw shape of the desired occlusion device. Clamping surface 16 can be relatively smooth, as shown, or alternatively can be textured with, for example, repeating patterns of bumps, protrusions or other irregularities known in the art to provide additional traction with a clamped vessel.

Cushion 14 is secured to attachment member 12 at the surface of the cushion opposite the clamping surface. The attachment member generally provides a rigid backing for the cushion as well as means for attachment of the cushion to the jaw of a clamp. Attachment member 12 can be made of a hard plastic, such as polycarbonate, or of metal. Means for attaching the attachment member to the jaw can comprise, for example, a pair of protrusions (not shown) that can be detachably coupled to recesses on the jaw. Other conventional means of attachment may also be employed. Alternatively, the cushion can be directly secured to a clamp jaw by means described in U.S. application Ser. No. 09/336,161, now U.S. Pat. No. 6,228,104 filed Jun. 18, 1999, Ser. No. 09/594,291 filed Jun. 15, 2000 and Ser. No. 09/491,237 now U.S. Pat. No. 6,273,902 filed Jan. 25, 2000 entitled "Surgical Clamp Having Replaceable Pad," each commonly owned by the assignee of the present application and incorporated herein in its entirety. Briefly, such means include a flexible elongate attachment member configured to be received in an elongate cavity or channel that extends longitudinally of a clamp jaw. Such attachment members can be formed of plastic that is flexible but generally stiffer and markedly less deflectable than the cushion material, such as nylon or polypropylene. This design is especially advantageous in that the resultant insert can accommodate a variety of jaw shapes and configurations, including curved jaws.

Deflecting element 20 is embedded in cushion 14 and includes elongate plate 22 embedded within the cushion with columns 24 extending from the plate. As shown in FIGS. 1 and 2, plate 22 extends longitudinally within the cushion in a plane generally parallel to clamping surface 16. Columns 24 extend from plate 22 in a direction generally perpendicular to the plate and the clamping surface, and include portions 26 extending from the clamping surface itself. Columns 24 are arranged in two parallel rows, with the columns within each row spaced uniformly, but it will be understood that the invention also contemplates other arrangements of columns.

Deflecting element 20 can be formed of a variety of materials, provided such materials are flexible but less deflectable than the cushion material. Suitable materials include metals, and plastics, such as nylon or polypropylene.

Insert 10 can be assembled in ways known in the art. For ease of manufacture, it is desirable to employ a process where attachment member 12 and deflecting element 20 are first provided, and then cushion 14 is overmolded onto the attachment member and deflecting element. Alternatively, the cushion can be overmolded onto the deflecting element and secured to the attachment member by other means, such as adhesive bonding or the like. Other methods of assembling the insert according to the invention will be readily apparent to those skilled in the art.

In operation, cushion 14 engages a vessel at clamping surface 16 and the cushion deflects and deforms to accommodate the vessel as a clamping force is applied. Extending portions 26 of columns 24, which also engage the vessel, are less deflectable than the cushion, and therefore provide localized areas of resistance to deformation along the cushion surface. These localized areas of resistance provide for increased traction between the pad and the vessel, thereby improving gripping of the vessel. At the same time, pressure from the engaged vessel against the columns, together with pressure against the cushion surface, is transmitted to the deflecting plate, which in turn transmits pressure and causes deflection of the cushion area beneath the deflecting plate, that is, that portion of the cushion between the deflecting plate and the clamp jaw. As a result, the entire deflecting element 20 itself deflects. The end result is that while the extending portions 26 provide improved gripping of the vessel, there is some deflection of these portions and the entire deflecting element 20 itself to minimize trauma to the vessel. In this manner, the inserts of the present invention are less traumatic than, for example, the device of U.S. Pat. No. 3,746,002 to Haller, which has pin members embedded in a cushion that are exposed under clamping, but which are rigid and non-conforming to the clamped vessel.

FIG. 3 shows a variation of the embodiment of FIGS. 1 and 2, which shows insert 10a that similarly includes cushion 14a and embedded deflecting element 20a comprising elongate plate 22a and columns 24a extending from the plate. However, columns 24a terminate near to but below clamping surface 16a. While in this variation, the columns do not extend from the clamping surface themselves, they still operate to provide localized areas of resistance to cushion deformation, and therefore provide similar gripping characteristics as the embodiment of FIGS. 1 and 2.

FIG. 4 shows a second embodiment of the invention. Like the embodiment of FIGS. 1 and 2, insert 10b includes deflecting element 20b embedded in cushion 14b, with the deflecting element comprising an elongate plate 22b having columns 24b extending therefrom. In this embodiment, however, one end of plate 22b is maintained in a fixed relationship to attaching structure 12b. As shown, strut 28 extends from attaching structure 12b and is fixedly secured to one end of plate 22b.

In this embodiment, the degree of deflection of plate 22b under a clamping load increases along the length of plate, from minimal deflection at the end fixed to strut 28 to maximal deflection at the end of the plate furthest from the strut. The result is that the deformability of the cushion as a whole varies along the length of the cushion. In operation, such variation provides greater flexibility in vessel occlusion, as the relative degree of deformation and corresponding resistance to such deformation can be controlled by adjusting clamping position of the vessel along the cushion length.

FIGS. 5 and 6 show a third embodiment of the invention. Insert 30 likewise includes cushion 34 secured to attachment member 32. The deflecting element is embedded in the cushion and is in the form of a helical coil 40 oriented longitudinally along the cushion length. Portions 46 of the coil extend from clamping surface 36 of the cushion. The attachment member, cushion and deflecting element can be made and assembled using materials and according to methods previously described above with respect to the first embodiment.

In operation, the insert of this embodiment functions much like that of the first embodiment. Extending portions 46 of coil 40 provide localized areas of resistance to deformation along the cushion surface and provide for increased traction between the insert and a clamped vessel. However, under clamping load the coil 40 will deflect within the cushion in the same manner as described for the deflecting plate of the first embodiment. Also, in this embodiment, depending on the number of coil turns, the extending portions 46 of the coil generally extend more or less transverse to the cushion length. This orientation of the extending portions further resists movement of a clamped vessel in directions along the cushion length.

FIGS. 6 and 7 show a fourth embodiment of the invention. Insert 60 includes cushion 54 secured to attachment member 52 and a deflecting element embedded in the cushion. The deflecting element in this embodiment is a fan-like arrangement comprising a series of folded pleats 60 extending longitudinally along the cushion length. Portions 66 of the pleats extend from clamping surface 66 of the cushion. The attaching structure, cushion, and deflecting element also can be made and assembled using materials and according to methods previously described above with respect to the first embodiment.

In operation, the insert of this embodiment again functions much like that of the first embodiment. Extending portions 66 of the folded pleats 60 also provide localized areas of resistance to deformation along the cushion surface and as well provide for increased traction between the insert and a clamped vessel. Under clamping load the pleats 60 will also deflect within the cushion in the same manner as previously described. Also, in this embodiment the extending portions 66 of the pleats 60 extend from the cushion surface transverse to the cushion length. As with the third embodiment described above, this orientation of extending portions 66 also resists movement of a clamped vessel in directions along the cushion length.

Although only certain embodiments have been illustrated and described, those having ordinary skill in the art will understand that the invention is not intended to be limited to the specifics of any of these embodiments, but rather is defined by the accompanying claims.

What is claimed is:

1. An insert for attachment to a jaw of a jaw-type occlusion device, comprising:

an attaching structure for attaching the insert to the jaw;

an elastomeric cushion secured to the attaching structure, the cushion having a clamping surface for engagement with a vessel of other body tissue, and a deflecting element having at least a portion thereof embedded within the cushion between the attaching structure and the clamping surface, and wherein said deflecting element further comprises a coil oriented longitudinally along the length of the cushion.

2. The insert of claim 1 wherein portions of the coil extend from the cushion surface.

3. An insert for attachment to a jaw of a jaw-type occlusion device, comprising:

an attaching structure for attaching the insert to the jaw;

an elastomeric cushion secured to the attaching structure, the cushion having a clamping surface for engagement with a vessel or other body tissue, and a deflecting element having at least a portion thereof embedded within the cushion between the attaching structure and the clamping surface, and wherein said deflecting element further comprises folded pleats extending longitudinally along the cushion length, and wherein portions of the pleats extend from the cushion surface.

* * * * *